United States Patent
Oh

(10) Patent No.: US 9,249,159 B2
(45) Date of Patent: Feb. 2, 2016

(54) COMPOSITION FOR TREATING HEPATITIS C VIRUS, REGULATING PHOSPHORYLATION OF REPLICASE

(75) Inventor: Jong-Won Oh, Goyang-si (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 14/130,107

(22) PCT Filed: Apr. 23, 2012

(86) PCT No.: PCT/KR2012/003102
§ 371 (c)(1),
(2), (4) Date: Apr. 9, 2014

(87) PCT Pub. No.: WO2013/002484
PCT Pub. Date: Jan. 3, 2013

(65) Prior Publication Data
US 2014/0219960 A1    Aug. 7, 2014

(30) Foreign Application Priority Data
Jun. 30, 2011 (KR) .................. 10-2011-0064654

(51) Int. Cl.
| | | |
|---|---|---|
| A61K 31/44 | (2006.01) | |
| A61K 31/70 | (2006.01) | |
| C07D 513/04 | (2006.01) | |
| A61K 31/4184 | (2006.01) | |
| A61K 31/47 | (2006.01) | |
| A61K 31/519 | (2006.01) | |
| A61K 31/55 | (2006.01) | |
| A61K 31/4433 | (2006.01) | |
| A61K 31/444 | (2006.01) | |
| A61K 31/395 | (2006.01) | |
| A61K 31/4409 | (2006.01) | |
| A61K 31/451 | (2006.01) | |
| A61K 31/4545 | (2006.01) | |
| A61K 38/21 | (2006.01) | |
| C07D 211/64 | (2006.01) | |
| C07D 213/75 | (2006.01) | |
| C07D 215/38 | (2006.01) | |
| C07D 235/08 | (2006.01) | |
| C07D 401/12 | (2006.01) | |
| C07D 405/12 | (2006.01) | |
| A61K 31/7048 | (2006.01) | |

(52) U.S. Cl.
CPC ............ *C07D 513/04* (2013.01); *A61K 31/395* (2013.01); *A61K 31/4184* (2013.01); *A61K 31/44* (2013.01); *A61K 31/444* (2013.01); *A61K 31/4409* (2013.01); *A61K 31/4433* (2013.01); *A61K 31/451* (2013.01); *A61K 31/4545* (2013.01); *A61K 31/47* (2013.01); *A61K 31/519* (2013.01); *A61K 31/55* (2013.01); *A61K 38/212* (2013.01); *C07D 211/64* (2013.01); *C07D 213/75* (2013.01); *C07D 215/38* (2013.01); *C07D 235/08* (2013.01); *C07D 401/12* (2013.01); *C07D 405/12* (2013.01); *A61K 31/7048* (2013.01)

(58) Field of Classification Search
CPC .................. A61K 31/529; A61K 31/7048
USPC ..................................... 514/300, 29
See application file for complete search history.

(56) References Cited

U.S. PATENT DOCUMENTS

| | | | |
|---|---|---|---|
| 6,605,614 B2 | 8/2003 | Bachand et al. | |
| 7,803,831 B2 | 9/2010 | Beswick et al. | |
| 8,367,836 B2 * | 2/2013 | Xu et al. | 546/268.1 |
| 2009/0318427 A1 | 12/2009 | Dennison et al. | |

FOREIGN PATENT DOCUMENTS

WO    WO-09153516 A1    12/2009

OTHER PUBLICATIONS

Kim et al. "Suppression of Hepatitis C Virus Replication by Protein Kinase C-Related Kinase 2 Inhibitors That Block Phosphorylation of Viral RNA Polymerase." *J. Viral Hepatitis.* 16(2009):697-704.

* cited by examiner

*Primary Examiner* — Kevin E Weddington
(74) *Attorney, Agent, or Firm* — Mintz Levin Cohn Ferris Glovsky and Popeo, P.C.; Fred C. Hernandez; Linyu L. Mitra

(57) ABSTRACT

The present invention relates a novel composition for preventing or treating hepatitis C virus, regulating the phosphorylation of a replicase. More specifically, it is possible to prevent or treat hepatitis C using a novel PRK2 inhibitor discovered through structure modeling, and to prevent or treat hepatitis C, particularly, interferon-insensitive hepatitis C through coadministration of an Hsp90 inhibitor.

4 Claims, 8 Drawing Sheets

COMPOSITION FOR TREATING HEPATITIS C VIRUS, REGULATING PHOSPHORYLATION OF REPLICASE

CROSS-REFERENCE TO RELATED APPLICATION

This application is a national stage application, filed under 35 U.S.C. §371, of International Application No. PCT/KR2012/003102, filed Apr. 23, 2012, which claims priority to and the benefit of Korean Patent Application No. 2011-0064654, filed Jun. 30, 2011, the disclosures of which are incorporated herein by reference in their entirety.

BACKGROUND

1. Field of the Invention

The present invention relates to a novel composition for preventing or treating hepatitis C virus capable of effectively inhibiting replication of virus by regulating stability and activity of kinase involved in phosphorylation of replicase of hepatitis C virus.

2. Discussion of Related Art

Hepatitis C virus (HCV) is the major etiologic agents of non-A and non-B hepatitis. More than 170 million people worldwide are chronically infected with HCV. Persistent HCV infection establishes a chronic hepatitis that can lead to liver cirrhosis and hepatocellular carcinoma. Further, the combined administration of IFN-α injection with ribavirin currently used as the standard HCV therapy is limited in use due to its serious side effects. Furthermore, IFN-α is effective in less than about 50% of genotype 1 HCV-infected patients. Therefore, various therapeutic options have been under investigation in order to develop effective and specific therapies with the least toxicity.

The HCV has a positive-sense single stranded RNA genome of approximately 9.6 kb, which consists of one long open reading frame (ORF) flanked by untranslated regions (UTRs) at both the 5' and 3' ends of the genome. The ORF encodes a single polyprotein that is proteolytically processed by cellular and viral proteases into at least 10 functional viral proteins, including both structural and nonstuructural proteins. A HCV NS5B protein of 65 kDa, responsible for RdRp (RNA-dependent RNA polymerase) activity, is the key enzyme essential for HCV RNA replication.

According to preceding research, it was found that viral RNA polymerase is phosphorylated by PRK2 (protein kinase C-related kinase 2) and inhibition of PRK2 activity by a PRK2 inhibitor leads to effective inhibition of HCV replication.

Meanwhile, heat shock protein 90 (Hsp90) protects various cellular client proteins from proteasomal degradation through interactions with the cellular client proteins and also exhibits additional functions. The Hsp90 was identified as a host factor essential for maturation of viral protein. Recently, it was proved that the Hsp90 forms a trimeric complex with HCV NS5A and FKBP9, a cyclophilin family immunophilin, to regulate HCV RNA replication. Furthermore, it was found that as Hsp90 inhibitors, 17-AAG (17-allyaminogeldanamycin) and 17-DMAG (17-(dimethylaminoethylamino)-17-demethoxygeldanamycin), which are analogues of geldanamycin as a benzoquinone ansamycin antibiotic, inhibit HCV replication in cellular-based assays using HCV replicons and in HCV-infected chimeric mice with trans-humanized liver. However, a precise role of the Hsp90 in HCV replication remains unknown. The Hsp90 helps folding of various client proteins. One of its putative clients is PDK1 (3-phosphoinositide-dependent kinase-1). However, destabilization of the PDK1 was not observed in breast cancer lines, suggesting a cell-type dependent differential regulation of the PDK1 stability by Hsp90 inhibition.

It was proved by the present inventors that the PDK1 is an upstream kinase of PRK2 and the PRK2 is a cellular kinase responsible for HCV NS5B phosphorylation. Thus, the present inventors completed the present invention by analyzing whether Hsp90 inhibition leads to an inhibitory effect on HCV replication by affecting the phosphorylation of the NS5B protein.

SUMMARY OF THE INVENTION

The present invention is directed to providing a composition for preventing or treating hepatitis C virus through discovery of a novel PRK2 inhibitor having excellent efficacy and confirming a hepatitis C virus replication inhibition effect by inhibition of Hsp90.

One aspect of the present invention provides a composition for preventing or treating hepatitis C virus comprising a compound expressed by Chemical Formula 1 below:

[Chemical Formula 1]

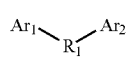

In Chemical Formula 1, $Ar_1$ represents aryl or nitrogen-containing heteroaryl having 5 to 24 carbon atoms, or a nitrogen-containing substituted heterocyclic having 3 to 12 carbon atoms, $R_1$ represents alkyl having 1 to 10 carbon atoms substituted with —NH—(O)— or nitrile, and $Ar_2$ represents cycloalkyl having 3 to 12 carbon atoms, a nitrogen-containing substituted heterocyclic having 3 to 12 carbon atoms, nitrogen-containing heteroaryl having 5 to 24 carbon atoms, heteroaryloxy containing at least one of oxygen, nitrogen, and sulfur atoms and having 5 to 24 carbon atoms substituted or unsubstituted with aryl having 5 to 24 carbon atoms, or aryl having 5 to 24 carbon atoms substituted with —NH—(O)—$R_2$. Herein, the $R_2$ represents alkyl having 1 to 10 carbon atoms.

BRIEF DESCRIPTION OF THE DRAWINGS

The above and other objects, features, and advantages of the present invention will become more apparent to those of ordinary skill in the art by describing in detail exemplary embodiments thereof with reference to the attached drawings, in which:

FIG. 3(A) illustrates a PRK2 phosphorylation inhibition effect of 17 PRK2 activity inhibitor candidates screened through structure modeling, FIG. 3(B) illustrates an effect of screened PRK2 inhibitors (#10, #11, #12, #13, and #17) on expression of HCV NS5B protein, and FIG. 3(C) illustrates HCV RNA titers in cells after treatment with screened PRK2 inhibitors (#11 and #17).

FIG. 9(C) illustrates a change in protein level in an R-1 cell after treatment with 17-DMAG, FIG. 9(D) provides an analysis result of an HCV genome copy number in an R-1 cell treated with 17-DMAG after pcDNA3.1-PRK2 is transfected with various concentrations, and FIG. 9(E) provides a Tet-induced vector (upper diagram) expressing HCV NS protein (NS3-NS5B) and a image (lower image) showing phosphorylated NS5B level in an Huh7TR-NS cell after treatment with 17-DMAG or HA1077.

FIG. 10(A) illustrates HCV RNA titers in an R-1 cell after single treatment of 17-DMAG and/or HA1077 or combined treatment with IFN-α, and FIG. 10(B) shows an effect of IFN-α on a PDK1-PRK2 signaling pathway.

FIG. 11(A) illustrates HCV RNA titers in an Huh7 cell infected with HCV after treatment with 17-DMAG or IFN-α, FIG. 11(B) provides a measurement result (lower graph) of a change in HCV IRES activity in an Huh7 cell transfected with a dual luciferase reporter system (upper diagram) after treatment with 17-DMAG, and FIG. 11(C) provides an analysis result of a change in a cell cycle of an Huh7 cell after treatment with 17-DMAG.

DETAILED DESCRIPTION OF EXEMPLARY EMBODIMENTS

Figure 1:
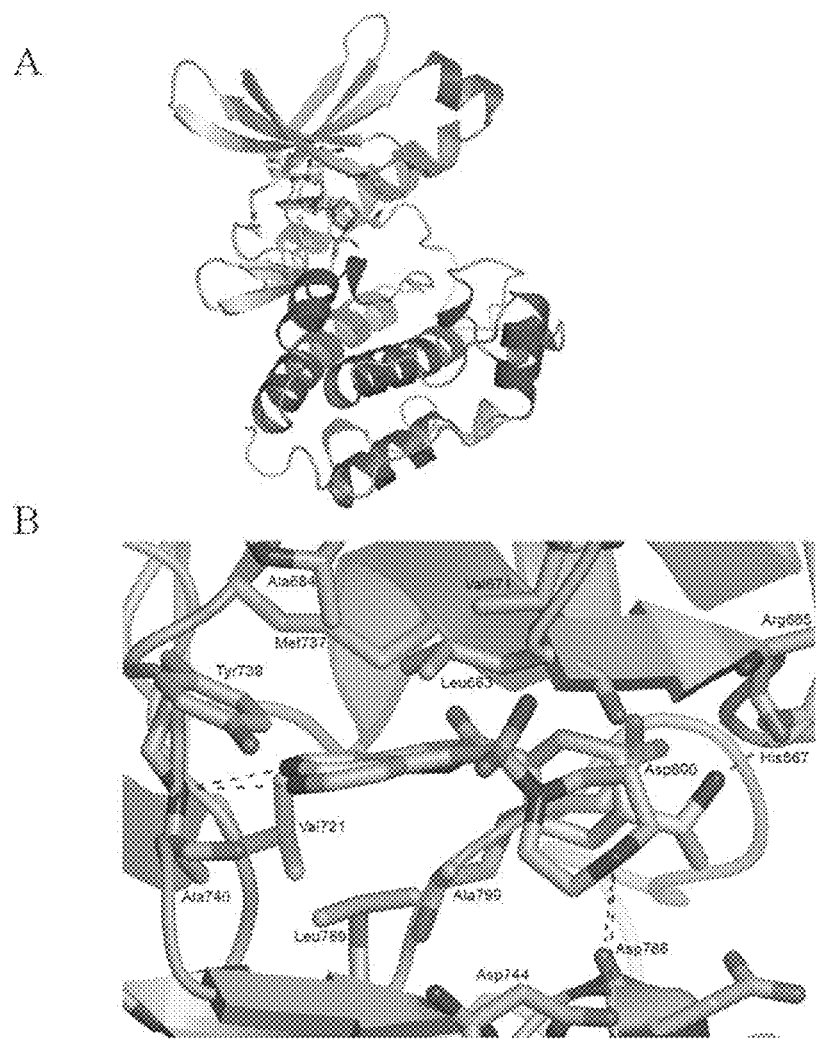
FIG. 1 illustrates a tertiary structure model of PRK2 through structure modeling (A) and the structure docking with Y27632 (B).

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements, components, and/or groups thereof, but do not preclude the presence or addition of one or more other features, integers, steps, operations, elements, components, and/or groups thereof.

With reference to the appended drawings, exemplary embodiments of the present invention will be described in detail below. To aid in understanding the present invention, like numbers refer to like elements throughout the description of the figures, and the description of the same elements will be not reiterated.

Hereinafter, exemplary embodiments of the present invention will be described in detail.

The present inventors completed the present invention by predicting a tertiary structure of PRK2 to discover a novel PRK2 activity inhibitor that has excellent efficacy and can be used as a medicine for HCV, screening a substance capable of docking with an active site of the PRK2 with the AutoDock-4 program, and discovering a novel PRK2 activity inhibitor through a docking experiment.

Therefore, the present invention provides a compound expressed by Chemical Formula 1 below as a novel composition for preventing or treating hepatitis C virus:

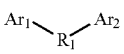

[Chemical Formula 1]

In Chemical Formula 1, $Ar_1$ represents aryl or nitrogen-containing heteroaryl having 5 to 24 carbon atoms, or a nitrogen-containing substituted heterocyclic having 3 to 12 carbon atoms, $R_1$ represents alkyl having 1 to 10 carbon atoms substituted with —NH—(O)— or nitrile, and $Ar_2$ represents cycloalkyl having 3 to 12 carbon atoms, a nitrogen-containing substituted heterocyclic having 3 to 12 carbon atoms, nitrogen-containing heteroaryl having 5 to 24 carbon atoms, heteroaryloxy containing at least one of oxygen, nitrogen, and sulfur atoms and having 5 to 24 carbon atoms substituted or unsubstituted with aryl having 5 to 24 carbon atoms, or aryl having 5 to 24 carbon atoms substituted with —NH—(O)—$R_2$. Herein, the $R_2$ represents alkyl having 1 to 10 carbon atoms.

The terms used to define substituents of the compound of the present invention are as follows.

The term "alkyl" refers to a linear, branched, or cyclic saturated hydrocarbon chain having 1 to 10 carbon atoms, unless context dictates otherwise. Examples of a $C_{1-10}$ alkyl group include, but are not limited to, methyl, ethyl, propyl, butyl, pentyl, hexyl, heptyl, octyl, nonyl, decyl, isopropyl, isobutyl, sec-butyl and tert-butyl, isopentyl, neopentyl, isohexyl, isoheptyl, isooctyl, isononyl, and isodecyl.

The term "cycloalkyl" refers to a nonaromatic saturated hydrocarbon ring having 3 to 12 carbon atoms and includes a mono ring and a fused ring, unless context dictates otherwise.

Representative examples of $C_{3-12}$ cycloalkyl include, but are not limited to, cyclopropyl, cyclobutyl, cyclopentyl, cyclohexyl, cycloheptyl, and cyclooctyl.

The term "nitrogen-containing heterocyclic" refers to a saturated or unsaturated (nonaromatic) group having 3 to 12 carbon atoms and includes a single ring or multiple condensed rings and at least one nitrogen atom in a cycle, and may be a fused bridge and spiro-ring system. In a fused ring system, one or more rings may be cycloalkyl, aryl, or heteroaryl, but the point of attachment is through a heterocyclic ring. In a specific example, a nitrogen atom and/or a sulfur atom of a heterocyclic group is optionally oxidized to provide N-oxide, sulfinyl, and sulfonyl.

The term "nitrogen-containing substituted heterocyclic" refers to the nitrogen-containing heterocyclic having 1 to 5 substituents selected from the group consisting of alkyl, substituted alkyl, oxo (=O), tioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl ester, cycloalkyl, substituted cycloalkyl, heteroaryl, substituted heteroaryl, heterocyclic, substituted heterocyclic, —$SO_2$-alkyl, and —$SO_2$-cycloakyl.

The term "aryl" refers to a monovalent aromatic carbocyclic group having 5 to 24 carbon atoms including a single ring (for example, phenyl) or multiple condensed rings (for example, naphthyl or anthryl) wherein condensed rings may or may not be aromatic (for example, 2-benzoxazolinone, 2H-1,4-benzoxazin-3(4H)-one-7-yl, and the like) provided that the point of attachment is at an aromatic carbon atom. Preferably, the aryl includes phenyl and naphthyl.

The term "heteroaryl" refers to an aromatic group having 5 to 24 carbon atoms and 1 to 4 heteroatoms including at least one of oxygen, nitrogen, and sulfur atoms within the ring. Such heteroaryl groups can have a single ring (for example, pyridinyl or furyl) or multiple condensed rings (for example, indolizinyl or benzothienyl) wherein the condensed rings may or may not be aromatic and/or contain a heteroatom provided that the point of attachment is through an atom of the aromatic heteroaryl group. In a specific example, a nitrogen atom of a heteroaryl group is optionally oxidized to provide N-oxide (N→O), sulfinyl, or sulfonyl. Preferably, the heteroaryl includes pyridinyl, pyrrolyl, indolyl, thiophenyl, and furanyl.

The term "heteroaryloxy" refers to —O-heteroaryl, and the heteroaryl is the same as defined in the present specification.

To be specific, in the compound expressed by Chemical Formula 1, $Ar_2$ represents aryl or nitrogen-containing heteroaryl having 6 to 10 carbon atoms, or a nitrogen-containing substituted heterocyclic having 6 to 10 carbon atoms, $R_1$ represents alkyl having 1 to 2 carbon atoms substituted with —NH—(O)—or nitrile, and $Ar_2$ represents cycloalkyl having 6 to 12 carbon atoms, a nitrogen-containing substituted heterocyclic having 6 to 12 carbon atoms, nitrogen-containing heteroaryl having 6 to 10 carbon atoms, heteroaryloxy containing at least one of oxygen, nitrogen, and sulfur atoms and having 6 to 10 carbon atoms substituted or unsubstituted with aryl having 6 to 10 carbon atoms, or aryl having 6 to 10 carbon atoms substituted with —NH—(O)—$R_2$. Herein, the $R_2$ represents alkyl having 1 to 2 carbon atoms.

To be more specific, the compound expressed by Chemical Formula 1 may be any one of 3-[(2-ethylbutanoyl)amino-N-(pyridine-4-yl)benzamide], cyclohexanecarboxylic acid (1H-benzoimidazole-5-yl)-amide, (3r,5r,7r)-N-(quinolin-5-yl)adamantane-1-carboxamide, 1-methyl-4-phenylpiperidine-4-carbonitrile), 2-oxo-N-4-pyridinyl-3-piperidinecarboxamide, N-(2-oxoazepan-3-yl)pyridine-4-carboxamide, 2-oxo-N-(pyridine-4-yl)-2H-chromene-3-carboxamide, 2-oxo-N-(4-pyridinyl)-1,2-dihydro-3-pyridinecarboxamide, 1-benzyl-2-oxo-N-(4-pyridinyl)-1,2-dihydro-3-pyridinecarboxamide, or 5-oxo-N-pyridine-4-yl-[1,3]thiazolo[3,2-a]pyrimidine-6-carboxamide.

The compound expressed by Chemical Formula 1 is obtained by screening a substance docking with a PRK2 active site with the FlexX-Pharm program of Sybyl 7.2 modeling package produced by Tripos, Inc., and the compound can inhibit phosphorylation of NS5B protein of hepatitis C virus by inhibiting phosphorylation of PRK2 by inhibiting of PRK2 activity and can be used as a medicine for preventing or treating hepatitis C virus since the inhibition of phosphorylation of NS5B protein inhibits replication of virus.

Further, the composition for preventing or treating hepatitis C virus of the present invention may further include an Hsp90 (Heat Shock Protein 90) inhibitor.

The Hsp90 inhibitor inactivates Hsp90 activity and promotes degradation of an upstream kinase PDK1 to reduce phosphorylated PRK2, thereby destabilizing PRK2. The reduction in amount and activity of the PRK2 induces inhibition of phosphorylation of HCV NS5B and thus inhibits replication of HCV.

Therefore, combined administration of the PRK2 inhibitor containing the compound expressed by Chemical Formula 1 with the Hsp90 inhibitor is a double hit strategy for inhibiting replication of hepatitis C virus and has a remarkably excellent treatment effect as compared with a case where each of these inhibitors is administered alone.

According to an exemplary embodiment, the combined administration of the PRK2 inhibitor with the Hsp90 inhibitor has an effect similar to an effect of inhibiting replication of hepatitis C virus in the case of single treatment of IFN-α. Therefore, it can have an effective treatment effect in patients infected with hepatitis C virus insusceptible to IFN-α.

As the Hsp90 inhibitor, 17-AAG (17-allyaminogeldanamycin), 17-DMAG (17-(dimethylaminoethylamino)-17-demethoxygeldanamycin), or the like may be used alone or in combination of two or more thereof, but the present invention is not limited thereto.

Further, according to another exemplary embodiment, the combined administration of the PRK2 inhibitor or the Hsp90 inhibitor and the IFN-α has a 90% or higher effect of inhibiting replication of hepatitis C virus as compared with a control. Furthermore, the combined administration of the PRK2 inhibitor with the Hsp90 inhibitor has an anti-HCV effect equivalent to an effect in the case of single treatment of IFN-α.

Therefore, the composition for preventing or treating hepatitis C virus of the present invention can prevent and treat hepatitis C virus by means of combined administration with the IFN-α. Further, as for a patient in which IFN-α cannot show a treatment effect, single administration or combined administration of the PRK2 inhibitor and the Hsp90 inhibitor can effectively control replication of virus.

Further, the composition for preventing or treating hepatitis C virus of the present invention can be mixed with pharmaceutically acceptable carriers or media. During the formulation, active components are added in an adequate amount in a preferable range.

The pharmaceutically acceptable carriers include carriers and vehicles typically used in the field of medicine, and specifically include, but may not be limited to, ion exchange resin, alumina, aluminum stearate, lecithin, serum protein (for example, human serum albumin), buffer substances (for example, various phosphates, glycine, sorbic acid, potassium sorbate, a partial glyceride mixture of saturated plant fatty acid), water, salt or electrolyte (for example, protamine sulfate, sodiumdihydrogen phosphate, potassium hydrogen phosphate, sodium chloride, and zinc salt), colloidal silica, magnesium trisilicate, polyvinyl pyrrolidone, a cellulose-based substrate, polyethylene glycol, sodium carboxymethyl cellulose, polyarylate, wax, polyethylene glycol, and wool fat, etc.

Further, the composition according to the present invention may further include a lubricating agent, a wetting agent, an emulsifying agent, a suspension, or a preservative agent in addition to the above-described components.

In one aspect, the composition according to the present invention may be manufactured in the form of a water-soluble solution for parenteral administration, and preferably, Hank's solution, Ringer's solution, or a buffer solution such as physically buffered salt water may be used. A water-soluble injection suspension may be added with a substrate capable of increasing viscosity of the suspension, such as sodium carboxymethyl cellulose, sorbitol, or dextran.

In another preferable aspect, the composition of the present invention may be manufactured in the form of pharmaceutical formulation for sterile injection of a water-based or oil-based suspension for sterile injection. Such a suspension can be formulated according to the technique publicly known in the art by using a suitable dispersing agent or wetting agent (for example, Tween 80) and a suspending agent.

Further, the pharmaceutical formulation for sterile injection may be a parenterally acceptable, nontoxic diluent or a sterile injection solution or suspension in a solvent (for example, a solution in 1,3-butanediol). As applicable vehicle and solvent, mannitol, water, Ringer's solution, and an isotonic sodium chloride solution may be used. Further, sterilized non-volatile oil is typically used as a solvent or a suspending medium. For this purpose, any mild non-volatile oil including synthesized mono- or diglyceride may be used.

Hereinafter, the present invention will be described in detail by means of Examples. However, it should be understood that the following Example are given by way of illustration of the present invention only, and are not intended to limit the scope of the present invention.

EXAMPLE 1

Discovery of Novel PRK2 Inhibitor

In order to discover a novel PRK2 inhibitor which has improved efficacy and can be used as a medicine for HCV, a tertiary structure of PRK2 protein was predicted. The tertiary structure of PRK2 protein was predicted by using a similar structure of PKA with the Modeller program of an InsightII software package. The predicted model underwent energy minimization until an energy gradient became lower than 0.1 kcal/mol with the Discover program. The final model was evaluated with the Profile 3D and PROCHECK program. Then, a docking experiment was carried out with the AutoDock-4 program. The final docking model was obtained by using a PyMol package (http://pymol.sourceforge.net).

FIG. 1B shows a structure docking with Y27632 having an inhibition effect similar to that of HA1077 currently and clinically used as a substance for inhibiting a predicted tertiary structure of PRK2 and activity of PRK2.

Then, 17 PRK2 inhibitor candidates were obtained by screening a substance docking with an active site of a PRK2 kinase with the FlexX-Pharm program of Sybyl 7.2 modeling package produced by Tripos, Inc.

EXPERIMENTAL EXAMPLE 1

Analysis of PRK2 Phosphorylation Inhibition Effect and Anti-HCV Efficacy After Treatment with Novel PRK2 Inhibitor In order to check a PRK2 phosphorylation inhibition effect of the novel inhibitors obtained in Example 1, R-1 cell line harboring HCV subgenomic replicons was used.

The R-1 cell line was comprised of cis-acting RNA elements of 5' and 3'-end untranslated regions (UTR) essential for replication of HCV RNA, a selection marker inserted to select a replicated RNA into a portion from which a structural protein coding site was removed, and a non-structural protein (NS3-NS5B)-coding gene required for replication. In the replicon, the selection marker was expressed by the HCV 5'-UTR and internal ribosome entry site (IRES) as a part of a coding gene of a core protein as a structural protein and capsid protein, and HCV non-structural proteins were expressed by IRES of EMCV. In order to obtain replicon cells, a HCV subgenomic replicon RNA was obtained by means of in vitro transcription by using a T7 RNA polymerase, free ribonucleotide was removed by using a spin column, and introduced into a hepatocellular carcinoma cell line by electroporation. In the presence of G418, a stable cell line, i.e. a cell line showing a resistance to G418 through replication of HCV subgenome, was obtained. Expression of the HCV non-structural proteins in this cell line was analyzed by Western blot to confirm that replication was being carried out, and the R-1 cell line was constructed. It was observed that an HCV RNA copy number was about $10^7$ copies/mL by a quantitative real-time PCR analysis using a TaqMan probe. The R-1 cell line was a cell line in which HCV RNA replication was being carried out, and thus it could be used to evaluate an HCV replication inhibition effect of a PRK2 activity inhibitor.

After the R-1 cell line was treated with the PRK2 inhibitor at a final concentration of 10 or 20 μM for 48 hours, phosphorylation or not of $Thr^{816}$ residue essential for activity of PRK2 was analyzed by Western blot using a phospho-PRK2 antibody to measure an expression level of phosphorylated PRK2. Immunoblotting using an anti-α-tubulin antibody was carried out to check whether or not the same amount of protein was loaded.

Figure 2:
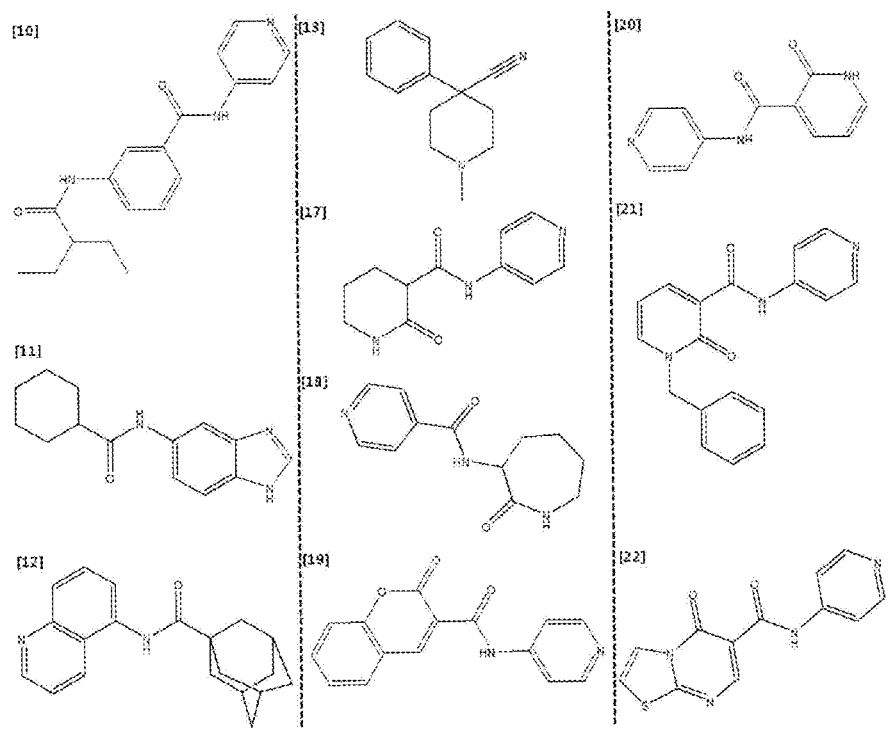
FIG. 2 illustrates novel PRK2 inhibitors according to the present invention.
Figure 3:
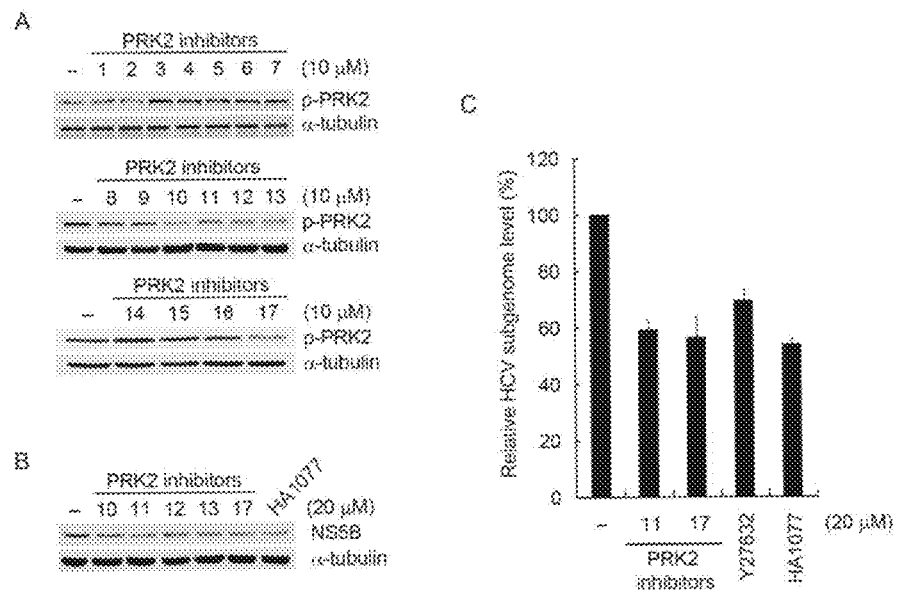
FIG. 3 illustrates anti-HCV activity of novel PRK2 inhibitors according to the present invention.

As a result, 5 compounds (#10, #11, #12, #13, and #17: structures illustrated in FIG. 2) showed a 50% or higher effect of inhibiting PRK2 phosphorylation (FIG. 3A).

Then, after the R-1 cell line was treated with each of 5 screened PRK2 inhibitors, HA1077 currently and clinically used as a PRK2 activity inhibitor, and Y27632 having a PRK2 activity inhibition effect at a final concentration of 20 μM for 48 hours, levels of HCV NS5B protein and HCV RNA in cell lysates (50 μg) were analyzed by Western blot and real-time RT-PCR.

As a result, it was observed that compounds #11 and #17 showed an HCV replication inhibition effect similar to that of HA1077 (FIGS. 3B and 3C).

Thereafter, an HCV replication effect of the novel PRK2 inhibitor in R-1 (FIGS. 4A and 4C) and a cell line infected with HCV (FIG. 4D) was analyzed.

To do so, after the two cell lines were treated with the compound #17 at higher concentrations (60 and 100 μM) than 20 μM for 48 hours, an HCV RNA genome level was checked by a real-time RT-PCR analysis. A value was a mean±standard deviation (SD) of three independent measurements. HCV RNA titer was quantified by real-time PCR analysis. Three independent experiments were performed in triplicate.

Figure 4:
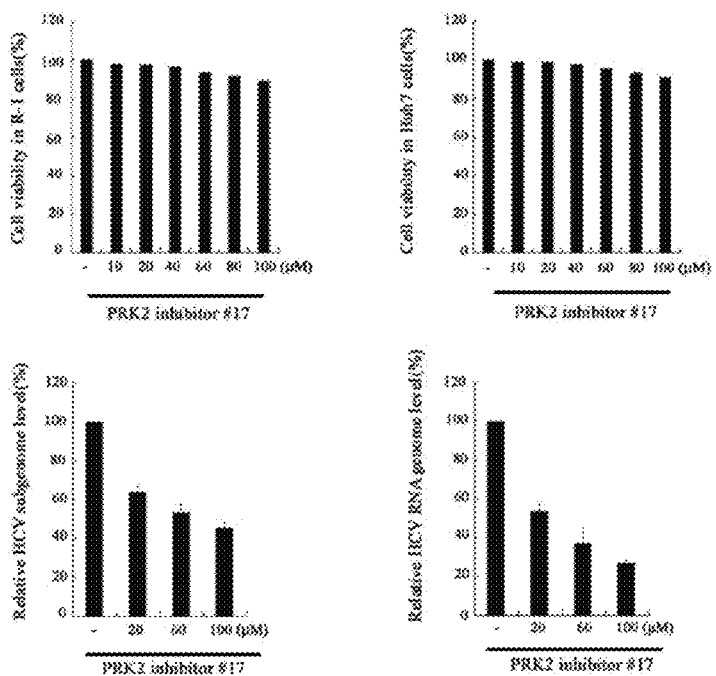
FIG. 4 illustrates cytotoxicity results after treatment of an R-1 cell (A) and a Huh7 cell (B) with a novel PRK2 inhibitor of the present invention, and also illustrates an HCV RNA replication inhibition effect in an R-1 cell (C) and a Huh7 cell (D) infected with HCV.

As shown in FIG. 4, it was confirmed that RNA titers were decreased in a dosage-dependent manner (FIGS. 4C and 4D), and it could be seen that the compound #17 for inhibiting PRK2 activity could be effectively used to inhibit HCV RNA replication and an efficacy of the compound #17 was slightly higher in a cell infected with JFH-1 than in an HCV subgenomic replicon cell. Further, it could be seen that when an R-1 cell (A) and a Huh7 cell (B) were treated with the screened compound #17 at a concentration of 100 µM, activity of the cells was not greatly inhibited.

Then, in order to test an HCV NS5B protein phosphorylation inhibition effect of the screened novel PRK2 inhibitor, in vitro kinase assay was carried out.

Using a recombinant active PRK2 and purified HCV NS5B protein as substrates, the screened inhibitors #11 and #17 were treated in the presence of gamma-$^{32}$P ATP and 100 µM ATP. The reaction mixture was separated by SDS-PAGE (8% gel), and a result thereof was checked by autoradiography.

Figure 5:
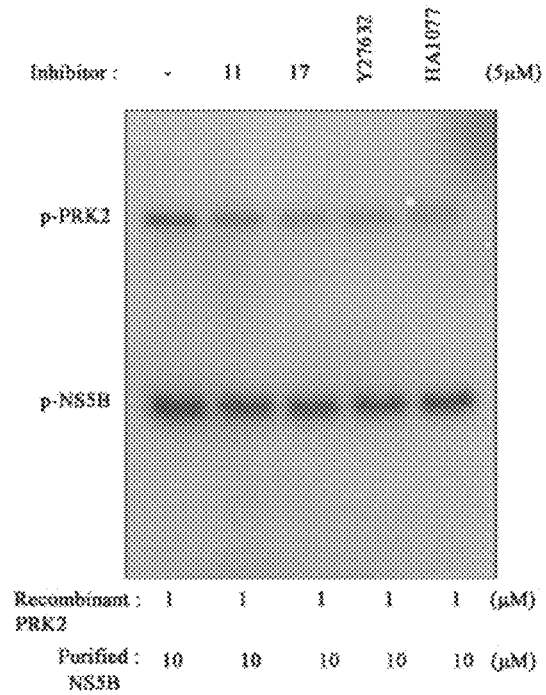
FIG. 5 illustrates an inhibitory effect on in vitro phosphorylation of NS5B protein after treatment with novel PRK2 inhibitors of the present invention.

As shown in FIG. 5, it could be confirmed that the compounds #11 and #17 inhibit phosphorylation of HCV NS5B protein, and the compound #11 had a similar level of inhibition effect as compared with conventional PRK2 activity inhibitors (HA1077 and Y27632). Thus, in the experiment carried out since then, derivatives of the PRK2 activity inhibitor #17 were produced for additional experiments.

5 derivatives (#18 to #22: refer to FIG. 2) were produced based on the inhibitor #17 showing the best effect. After the R-1 cell line was treated with each of these inhibitors or HA1077 and Y27632 at a final concentration of 20 µM for 48 hours, an HCV RNA genome level was checked by a real-time RT-PCR analysis and expressed in % with respect to a control treated with DSMO. Three independent experiments were conducted repeatedly three times. Data were expressed by mean±SD of the three experiments.

Figure 6:
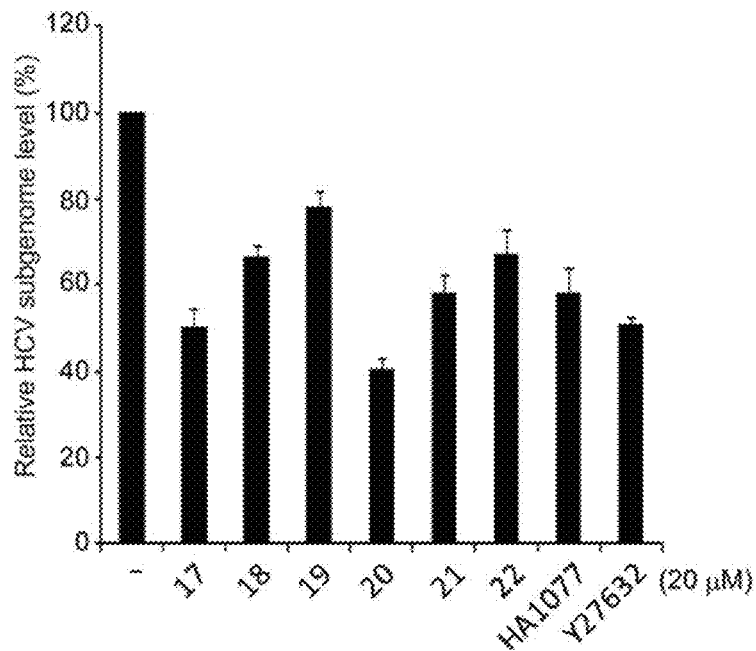
FIG. 6 illustrates effects of novel PRK2 inhibitors of the present invention, #17 compound derivatives on HCV RNA replication.

As shown in FIG. 6, HCV RNA titers were decreased by about 50% in the cell line treated with the inhibitor #17 and decreased by approximately 60% in the cell line treated with the inhibitor #20 as a derivative. The conventional PRK2 inhibitors, HA1077 and Y27632, showed inhibition effects of 40% and 49%, respectively. The inhibitor #20 as one of the derivatives of the inhibitor #17 showed the most excellent inhibition effect, and better effects could be observed as compared with the cases where the cell line was treated with HA1077 and Y27632 as inhibitors used in clinical tests.

Finally, PRK2 and HCV NS5B phosphorylation inhibition effects of the compounds #18, #19, #20, #21 and #22 as the derivatives of the compound #17 were analyzed through in vitro kinase assay.

A 1 µM recombinant PRK2 and 10 µM HCV NS5B were phosphorylated for 30 minutes in the presence of 10 µCi γ-$^{32}$P ATP and 100 µM ATP. The reaction mixture was separated by SDS-PAGE (8% gel), and a result thereof was checked by autoradiography.

Figure 7:
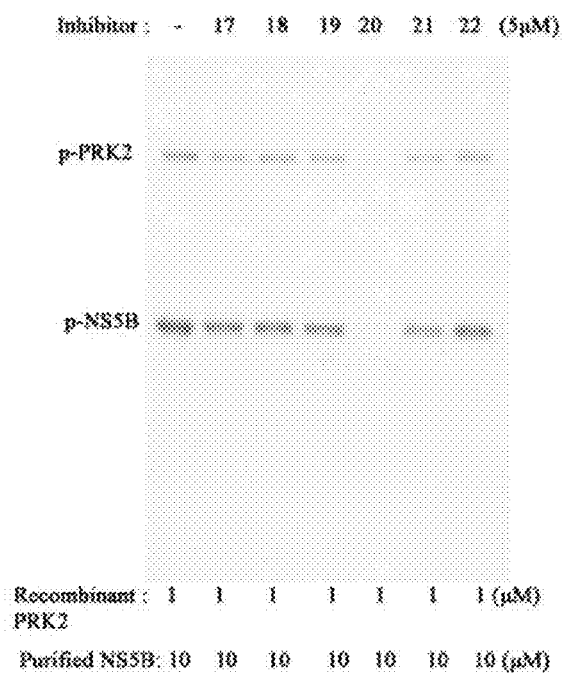
FIG. 7 illustrates an inhibition effect of novel PRK2 inhibitors of the present invention, #17 compound derivatives on in vitro phosphorylation of NS5B.

As shown in FIG. 7, the inhibitor #20 showed an excellent HCV replication inhibition effect as compared with the other derivatives. It could be observed that levels of the phosphorylated PRK2 and NS5B in the treated sample were decreased by approximately 80% as compared with a control.

EXAMPLE 2

Effect of Hsp90 on HCV Replication (Cell Culture and Reagent)

It was checked whether or not an effect of Hsp90 inhibition on HCV NS5B protein phosphorylation causes an HCV replication inhibition effect.

An hepatocellular carcinoma cell line Huh7 used to test an effect of Hsp90 on HCV replication was cultured in a Dulbecco's modified Eagle's medium (DMEM) supplemented with 10% fetal bovine serum (FBS), 2 mM L-glutamine, 1% penicillin/streptomycin, and 1% nonessential amino acids under standard culture conditions (5% $CO_2$, 37° C.).

The human hepatoma stable cell lines Huh7TR-4 and Huh7TR-NS [17], which express the tetracycline repressor and the HCV NS proteins (NS3-NS5) in a tetracycline-inducible manner, respectively, were maintained in the presence of blasticidin S (10 µg/mlL and Zeocine (100 µg/mL). NS protein expression in Huh7TR-NS was induced by addition of 1 µg/mL tetracycline for 24 h. The Huh7 cell-derived cell line R-1, supporting stable, autonomous replication of genotype 1b HCV subgenomic replicon RNA, was described previously. 17-DMAG, the PRK2 inhibitor, HA1077, and the inhibitor of phosphatidylinositol 3-kinase (PI3K), LY294002, were obtained from Sigma-Aldrich (St. Louis, Mo., USA) and Calbiochem Inc. (La Jolla, Calif., USA), and Biomol (Plymouth Meeting, Pa., USA), respectively. IFN-α was purchased from Sigma-Aldrich (1-4276).

(HCV Infection and Drug Treatment)

Full-length, infectious HCV RNA of the genotype 2a HCV clone JFH1 was prepared by in vitro transcription using the MEGAscript T7 kit (Ambion, Austin, Tex., USA) and electroporated into Huh7 cells as described previously. Briefly, at 72 h post electroporation, culture medium was collected, cleared by low-speed centrifugation, and passed through a 0.45-µm filter (Millipore, Billerica, Mass., USA) before being used for infection of Huh7 cells. Cells were infected with HCV at a multiplicity of infection of 0.3 by adsorption for 3 h with periodic rocking, then washed three times with phosphate-buffered saline (PBS) and maintained in complete DMEM. HCV subgenomic replicon cells or Huh7 cells infected with HCV (JFH1) were treated with 17-DMAG or PRK2 inhibitor alone or in combination with IFN-α (100 IU/ml) for 72 h.

(Cytotoxicity Assay)

Cytotoxicity of 17-DMAG was measured by using a reagent MTS [3-(4,5-dimethylthiazol-2-yl)-5-(3-carboxylmethoxyphenyl)-2-(4-sulfophenyl)-2H-tetrazolium] (Promega, Madison, Wis., USA) according to the protocols of the manufacturer. The experiment was carried out as follows.

Huh7 or R-1 cells ($2 \times 10^4$ cell/well) were seeded in a 96-well plate and treated with 17-DMAG at different concentrations for 72 hours. Then, the culture medium was removed and a MTS substrate dissolved in the culture medium containing 5% FBS was added to each well of the plate. The cells were cultured at 37° C. for 1 hour, and absorbance at 490 nm was read in a 96-well micro plate automatic reading system using GloMax-Multi detection system (Promega).

(Immunoblotting and Immunoprecipitation)

Total cell lysates from cells treated with inhibitors or IFN-α by using antibodies to PDK1, p-PDK1 (S241), PRK2, and p-PRK2 (T816) (products of Cell Signaling Technology, Inc., Beverly, Mass., USA) was used for immunoblotting. In order to detect PKC isoforms α, β, and γ, a polyclonal antibody to a consensus sequence present in three PKC (protein kinase C) isoforms α, β and γ (anti-pan-PKC; Zymed Laboratories, San Francisco, Calif., USA) was used. An anti-α-tubulin antibody (Oncogene Research Products, Cambridge, Mass., USA) was carried out in immunoblotting for checking whether or not the same amount of protein was loaded.

For co-immunoprecipitation experiment, the cells cells were resuspended in lysis buffer A (100 mM Tris-HCl, pH 8.0, 150 mM NaCl, 1% Triton X-100, 10 mM NaF, 1 mM $Na_3VO_4$, 17.5 mM β-glycerophosphate) supplemented with an EDTA-free protease inhibitor cocktail (Roche Applied Science, Indianapolis, Ind., USA) and incubated on ice for 30 min. After centrifugation, cell lysates (500 μg) and an anti-p-Ser antibody (clone PSR-45; Sigma-Aldrich) were incubated together. Immunoprecipitates, resolved by sodium dodecyl sulfate polyacrylamide gel electrophoresis (SDS-PAGE), were transferred to nitrocellulose membranes (Hybond-ECL; Amersham Biosciences, Piscataway, N.J., USA) and immunoblotted with anti-NS5B serum (Quantitative Real-Time RT-PCR)

Total RNA was extracted from R-1 or HCV (JFH1)-infected cells using TRIzol LS reagent (Invitrogen, Carlsbad, Calif., USA) and purified according to the manufacturer's instructions. HCV RNA levels were quantified by RT-PCR using a primer pair and TaqMan probe targeting a region within the HCV 5'-UTR as described previously. Cellular glyceraldehyde-3-phosphate dehydrogenase was used as an internal control. Assays were performed using the DyNAmo Probe 2-step qRT-PCR Kit (Finnzymes, Espoo, Finland) and a CHROMO4 continuous fluorescence detector (Bio-Rad, Hercules, Calif., USA), according to the manufacturer's instructions.

(Dual Luciferase Reporter Assay)

The dual luciferase expression vector allowing cap-dependent translation of a *Renilla* (RLuc) reporter and HCV internal ribosome entry site (IRES)-mediated luciferase translation of a firefly luciferase (FLuc) reporter was constructed by inserting the HCV IRES and partial core protein-coding region fused to the cDNA for FLuc downstream of the *Renilla* luciferase reporter gene as described previously. Huh7 cells were transiently transfected with the bicistronic dual luciferase vector using Fugene HD (Roche Applied Science, Indianapolis, Ind., USA). RLuc and FLuc activities in cell lysates were quantified using the Dual-Glo luciferase assay kit (Promega) on the GloMax-Multi detection system (Promega).

(Cell Cycle Analysis)

The Huh7 cell treated with 17-DMAG or HA1077 for 48 hours was collected and washed with PBS. The cells were fixed with chilled ethanol for 30 min, treated with RNase A (100 μg/ml) for 5 min at room temperature, stained with 50 μg/mL propidium iodide (PI, Sigma-Aldrich) for 30 min at 37° C., and analyzed using a FACS Calibur flow cytometer (Becton Dickinson, San Jose, Calif., USA).

EXAMPLE 3

Effect of Hsp90 Inhibitor on Stabilization and Activation of PDK1 and PRK2

Figure 8:
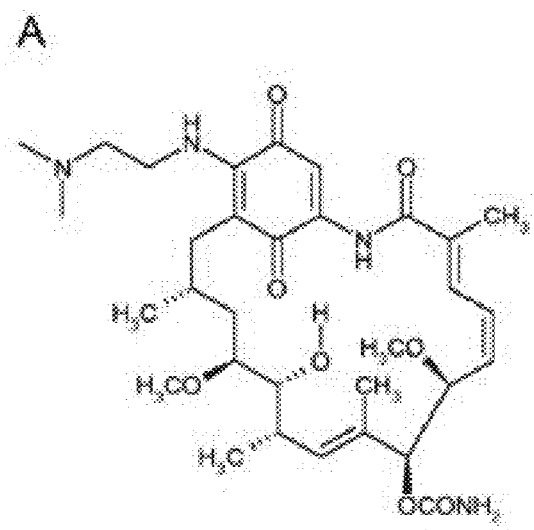
FIG. 8 illustrates a chemical structure of 17-DMAG (A) and stabilization and activation states of PDK1 and PRK2 in a Huh7 cell after treatment with 17-DMAG (B).
Figure 8:
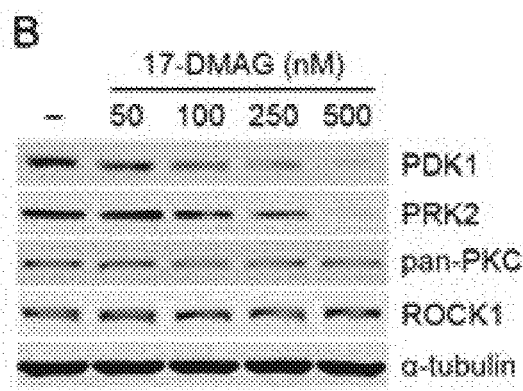

In order to test whether or not PDK1 in Huh7 as an HCC cell line was destabilized by inhibition of Hsp90, 17-DMAG as a second-generation geldanamycin derivative known as being safer than geldanamycin or its derivative 17-AAG and effective for oral delivery was used (FIG. 8A). The Huh7 cell was treated for 48 hours along with an increase in concentration of 17-DMAG, and a steady state level of PDK1 was evaluated by immunoblotting.

As shown in FIG. 8B, the treatment with 17-DMAG gradually and significantly decreased the PDK1 level. Further, it was observed that at 500 nM, the PRK2 level was decreased by about 68% as compared with the level of a non-treated control. As a result of immunoblotting on other kinases, for example, pan-PKC (α, β, and γ) and Rho-kinase I (ROCKI), steady state contents thereof were not significantly affected. This result showed that stabilization of PKC-α and PKC-γ was not regulated by Hsp90.

EXAMPLE 4

Effect of Hsp90 Inhibitor on Phosphorylation of HCV RdRp

An experiment was carried out to check whether or not 17-DMAG inhibited virus RNA replication in an R-1 cell in which autonomous replication of a genotype 1b HCV subgenomic replicon RNA was maintained. Before antiviral activity of 17-DMAG was evaluated, an MTS assay was carried out to evaluate whether or not the drug interfered with cell viability. To be specific, the R-1 cell loaded with a selective HCV subgenomic replicon (upper diagram) and its parental cell line Huh7 were treated with 17-DMAG at a certain concentration for 72 hours, and cell viability was evaluated by the MTS assay.

As shown in FIG. 9A, 17-DMAG did not show significant cytotoxicity with respect to the Huh7 cell until a concentration became 500 nM (inhibition of less than 15% at 500 nM). However, PDK1 and PRK2 were present at similar levels in the two cell lines, but the R-1 cell was more sensitive to 17-DMAG than the parental cell line Huh7 (FIG. 9B).

Therefore, anti-HCV activity of 17-DMAG in the R-1 cell was tested at a level lower than 50 nM. To do so, the R-1 cell was treated with a vehicle (0.25% DMSO) or 17-DMAG for 72 hours and the cell lysates (50 μg) and antibodies specific to the proteins were immunoblotted to measure levels of the proteins. An anti-α-tubulin antibody (lower end panel) was used as an internal loading control. The levels of the proteins were measured by densitometric analysis of immunoblot, and the phosphorylated amounts and relative intensities calculated with respect to PDK1 and PDK2 were converted with respect to α-tubulin signals and then quantitated. As a result of three independent experiments showing similar results, a representative blot picture was illustrated. It was observed that the levels of PDK1 and p-PRK2 in the R-1 cell treated with 17-DMAG at a final concentration of 10 or 50 nM were decreased (FIG. 9C), and in the case of treating the R-1 cell with 17-DMAG at a concentration of 50 nM, stability of PRK2 in the R-1 cell was not affected. The treatment of the R-1 cell with 17-DMAG effectively inhibited HCV RNA replication and showed an inhibition effect of about 50% at a concentration of 50 nM (second bar in FIG. 9D).

Further, after the R-1 cell transfected along with an increase in concentration of pcDNA3.1 vector (first and second bars in FIG. 9C) or pcDNA3.1-PRK2 was treated with a vehicle (0.25% DMSO, control) or 50 nM 17-DMAG for 72 hours, the cell was collected, and a level of HCV RNA remaining in the cell was analyzed. A relative HCV genome copy number was expressed in % with respect to a control treated with DSMO. Three independent experiments were conducted repeatedly three times. Data suggested were mean±SD values of the three independent experiments.

It was already observed that activated PRK2 were associated with improvement in HCV NS5B phosphorylation and HCV replication. 17-DMAG in the R-1 cell decreased stability of PDK1 and lowered a p-PRK2 level. Therefore, an ability of the Hsp90 inhibitor to inhibit NS5B phosphorylation was analyzed.

Figure 9:
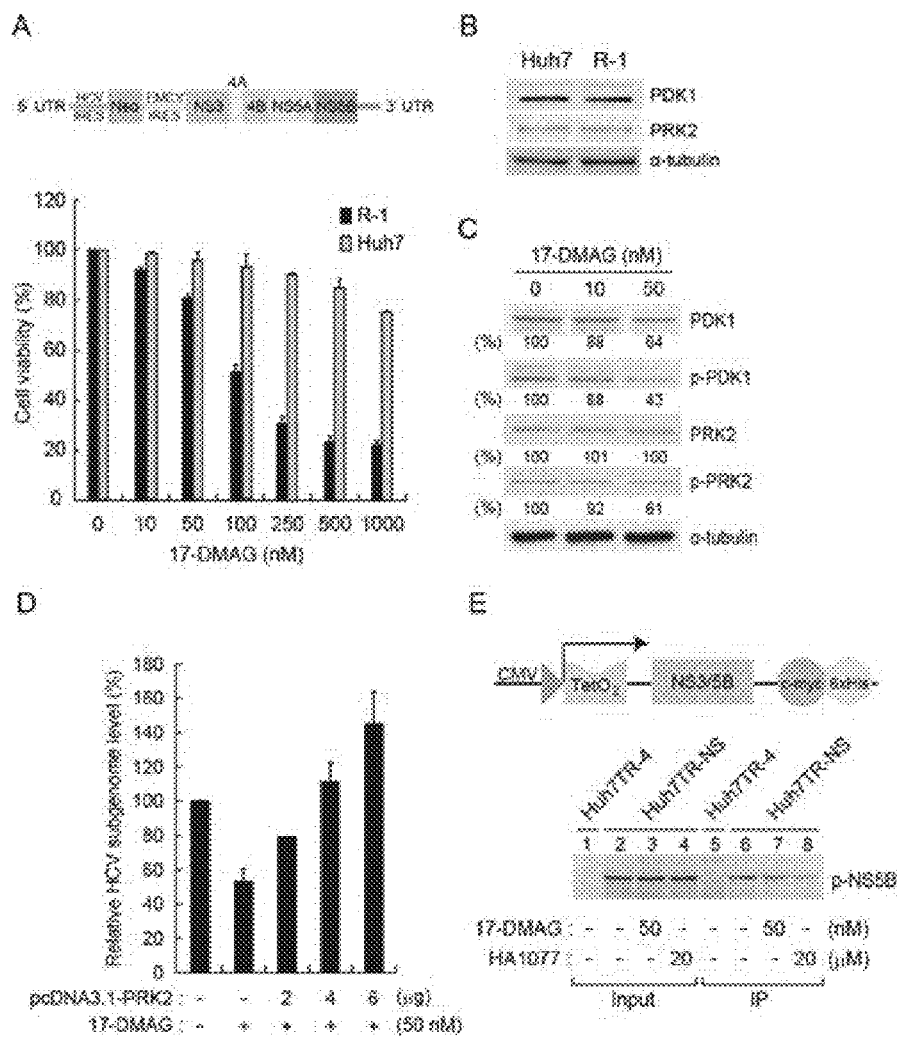
FIG. 9 illustrates an anti-HCV effect of 17-DMAG, and FIG. 9(A) provides an HCV subgenomic replicon (upper diagram) and a graph (lower graph) showing an effect of 17-DMAG on cell viability, FIG. 9(B) provides an analysis result of expression of PDK1 and PRK2 in Huh7 and R-1 cells.

To do so, an Huh7TR-NS cell (a schematic view of a Tet-induced vector expressing HCV NS proteins (NS3-NS5B) as shown in the upper end of FIG. 9) in which expression of HCV NS proteins did not occur together with virus RNA replication was cultured for 24 hours to induce expression of the NS proteins after 1 μg/mL of tetracycline was added to a medium. Then, treatment with 17-DMAG (50 nM) or HA1077 (20 μM), a PRK2 inhibitor, was carried out for 48 hours. Huh7TR-4 as a parental cell line of Huh7TR-NS did not express HCV NS proteins and was used as a control. The proteins in which amino acid serine was phosphorylated were immunoprecipitated from cell lysates by using an anti-phosphoserine antibody. The immunoprecipitated proteins (lanes 5 to 8) and 4% cell lysates (lanes 1 to 4) were immunoblotted with a purified polyclonal anti-NS5B antibody. A case without treatment with an inhibitor was expressed as (−).

As shown in FIG. 9E, as a result of immunoblotting after p-NS5B was immunoprecipitated by the anti-p-Ser antibody, it was shown that the treatment with 17-DMAG inhibited NS5B phosphorylation in the Huh7TR-NS cell expressing HCV NS proteins (compare lane 6 with lane 7). Further, it was confirmed that the treatment with HA1077 as a PRK2 inhibitor at a concentration of 20 μM also inhibited NS5B phosphorylation through inhibition of PRK2 activity (lane 8).

The above-described result shows that a replication inhibition effect of 17-DMAG in the R-1 cell in which HCV was replicated was caused by a PDK1-PRK2 signaling pathway and HCV replication was regulated through Hsp90 inhibition by PRK2 as a downstream kinase of PDK1.

EXAMPLE 5

HCV Replication Inhibition Effect of Combined Treatment with Hsp90 Inhibitor and IFN-α or PRK2 Inhibitor Combined administration of IFN-α with ribavirin has been used as the standard treatment method for treating HCV infection. In order to evaluate an ability of 17-DMAG that inhibits HCV replication when treated in combination with IFN-α an R-1 cell harboring a genotype 1b HCV subgenomic replicon was treated with 50 nM of 17-DMAG and 100 IU/mL of IFN-α. After 72 hours, an HCV subgenomic RNA level was analyzed by quantitative RT-PCR.

Figure 10:
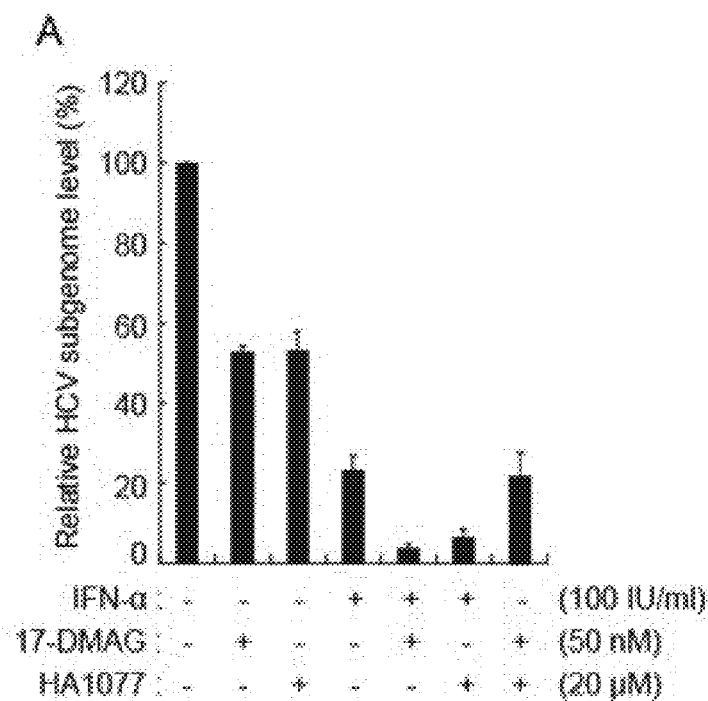
FIG. 10 illustrates an HCV replication inhibition effect after combined treatment with 17-DMAG and IFN-α or HA1077.
Figure 10:
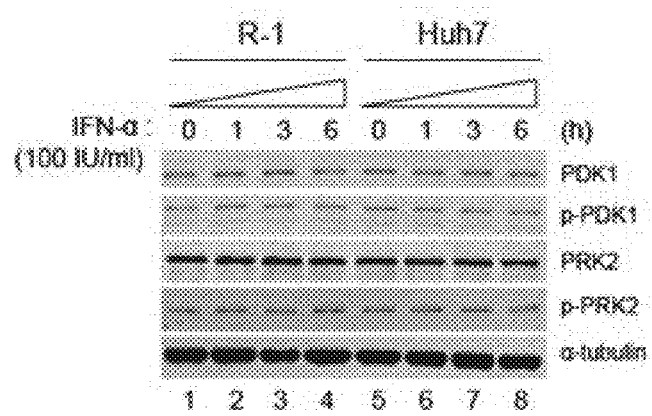

As shown in FIG. 10A, in the case of the treatment with 100 IU/ml of IFN-α alone, the content of HCV RNA was decreased by approximately 80%, whereas in the case of the combined treatment of 50 nM of 17-DMAG with IFN-α approximately a hundredfold decrease in viral RNA was induced. Further, in the case of the combined treatment of HA1077 (20 μM) with IFN-α (100 IU/ml), anti-HCV activity of IFN-α was improved. These results offer a remarkable evidence that the combined treatment of 17-DMAG with IFN-α is an effective strategy for inhibiting HCV replication. Further, in the case of the combined treatment of 17-DMAG (50 nM) and HA1077 (20 μM), virus replication was inhibited by approximately 80%, which was equivalent to an inhibition effect in the case of the treatment with 100 IU/ml of IFN-α alone. This suggests that the combined treatment prevents phosphorylation of HCV NS5B, thereby effectively inhibiting HCV replication.

Then, in order to check whether or not IFN-α affected a PDK1-PRK2 signaling pathway, the R-1 cell was treated with 100 IU/ml of IFN-α hourly for 6 hours. SDS-PAGE was carried out to the cell lysates, and immunoblotting was carried out. The immunoblotting with anti-α-tubulin antibody was used as an internal control for loading. A representative result from one of the three independent experiments showing a similar result was illustrated.

As shown in FIG. 10B, after the treatment with IFN-α, any significant change in p-PRK2 content or PRK2 content was not observed (refer to lanes 1 to 4). Further, any change in activation of PDK1 in the treated cell was not observed. These results suggest that the contents of PDK1 and PRK2 in the cell or stabilization and activation thereof were not affected by the treatment of the R-1 cell with IFN-α. A similar result was observed from the Huh7 cell (refer to lanes 5 to 8).

EXAMPLE 6

Observation of Anti-HCV Activity of Hsp90 Inhibitor in Cell Infected with HCV

In order to analyze whether or not 17-DMAG can inhibit replication in a cell infected with HCV, an experiment was carried out with the genotype 2a HCV infectious clone JFH1, which produces infectious virions in Huh7 or Huh7-derived cell lines. After JFH1 RNA was introduced into the Huh7 cell by electroporation, a collected culture supernatant was used as a virus infection sample, and the Huh7 cell cultured in 60 to 70% confluency in a 10 cm-plate was infected with the sample and treated with 50 nM of 17-DMAG alone or in combination with 100 IU/mL of IFN-α. After 72 hours, total cellular RNA was extracted and HCV remaining in the infected cell was analyzed by quantitative RT-PCR.

Figure 11:
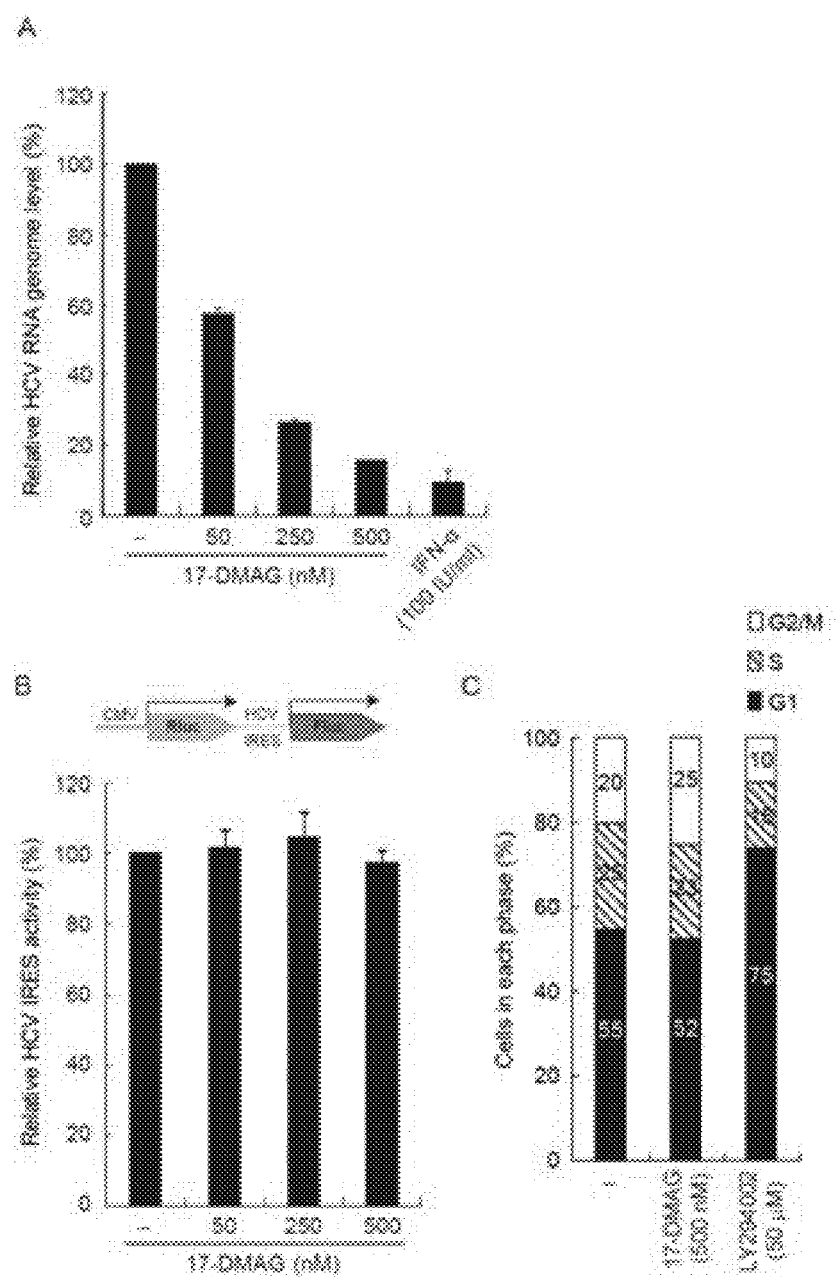
FIG. 11 illustrates an anti-HCV effect of 17-DMAG in genotype 2a HCV (JFH1)-infected cells.

As shown in FIG. 11A, it could be seen that in the case of the treatment with 500 nM of 17-DMAG, the level of the viral RNA was decreased by about 87%, and cell activity evaluated by the MTS assay at such a concentration was decreased by about 15%, and thus cell activity was not greatly inhibited (refer to FIG. 9A). This is comparable to an effect in the case of the treatment with 100 IU/mL of IFN-α alone in which about 90% of virus RNA replication was inhibited. Further, this result clearly shows that 17-DMAG can effectively inhibit HCV replication in a cell infected with genotype 2a HCV.

Then, in order to observe an effect of 17-DMAG on translation via HCV IRES, a dual reporter assay was carried out. The Huh7 cell was transfected by a dual reporter assay plasmid (FIG. 11B, upper diagram), and treated with 17-DMAG at various concentrations for 72 hours. A dual luciferase reporter was comprised of a CMV promoter, a firefly luciferase, an N-end part at a core-coding region constituting HCV IRES together with HCV 5'-UTR, and an HCV 3'-UTR from 5'-end in sequence. A level of the Firefly luciferase (cap-dependent translation) and a *Renilla* luciferase (translation via HCV IRES) was measured by dual luciferase assay and expressed in % with respect to a control treated with DMSO (first bar). Three independent experiments were conducted repeatedly three times. Data were expressed by mean±standard deviation of the three experiments.

As shown in FIG. 11B, 17-DMAG did not have an effect on the translation via HCV IRES.

Then, a cell cycle assay was carried out by using a flow cytometer. Huh7 cells were treated with DMSO (0.25%) or 500 nM of 17-DMAG for 48 hours, and a cell cycle thereof was analyzed by using a flow cytometer to show the percentage of cells in G1, S, and G2/M phases. LY294002 as a PI3K inhibitor was used as a positive control.

As shown in FIG. 11C, a cell cycle of the Huh7 cells treated with 500 nM of 17-DMAG was not significantly changed, whereas the LY294002, the PI3 kinase inhibitor, used as a positive control for the assay arrested a cell cycle in G1 phase as anticipated.

In conclusion, the present invention provides a novel mechanism for regulating HCV replication by Hsp90 inhibition. It was observed that 17-DMAG as an Hsp90 inhibitor destabilized PDK1 and PRK2, thereby effectively inhibiting HCV replication. This shows that Hsp90 plays an important role in regulating phosphorylation of HCV NS5B via a PDK1-PRK2 signaling pathway. The PDK1-PRK2 pathway is a potential target of an anti-HCV drug. Therefore, combined administration of an inhibitor targeting PDK1 or PRK2 or inhibitors targeting these kinases can be an effective treatment method for HCV. Further, a strategy for inhibiting HCV genome replication by inducing destabilization and deactivation of PDK1 and/or PRK2 may provide a successful treatment method for HCV.

The present invention is capable of effectively preventing or treating hepatitis C virus, particularly interferon-insensitive hepatitis C virus, by treating a novel PRK2 inhibitor and/or Hsp90 inhibitor based on the finding that replication of hepatitis C virus via a PDK1-PRK2 signaling pathway can be inhibited by inhibition of Hsp90.

The present invention can be used as a medicine for preventing or treating hepatitis C virus, particularly interferon-insensitive hepatitis C virus.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method for treating hepatitis C virus in a subject in need thereof comprising
administering to said subject a pharmaceutically effective amount of a PRK2 (Protein Kinase C-related Kinase 2) inhibitor,
wherein the PRK2 inhibitor is selected from the group consisting of: 3-[(2-ethylbutanoyl)amino-N-(pyridine-4-yl)benzamide], cyclohexanecarboxylic acid (1H-benzoimidazole-5-yl)-amide, (3r, 5r, 7r)-N-(quinolin-5-yl)adamantane-1-carboxamide, 1-methyl-4-phenylpiperidine-4-carbonitrile), N-(2-oxoazepan-3-yl)pyridine-4-carboxamide), 2-oxo-N-4-pyridinyl-3-piperidinecarboxamide, N-(2-oxoazepan-3-yl)pyridine-4-carboxamide, 2-oxo-N-(pyridine-4-yl)-2H-chromene-3-carboxamide, 2-oxo-N-(4-pyridinyl)-1,2-dihydro-3-pyridinecarboxamide, 1-benzyl-2-oxo-N-(4-pyridinyl)-1,2-dihydro-3-pyridinecarboxamide, and 5-oxo-N-pyridine-4-yl-[1,3]thiazolo[3,2-a]pyrimidine-6-carboxamide.

2. The method for treating hepatitis C virus of claim 1, wherein the PRK2 inhibitor is administered in combination with an Hsp90 (Heat Shock Protein 90) inhibitor.

3. The method for treating hepatitis C virus of claim 2, wherein the Hsp90 inhibitor is selected from the group consisting of 17-AAG (17-allyaminogeldanamycin), and 17-DMG (17-(dimethylaminoethylamino)-17-demethoxygeldanamycin).

4. The method for treating hepatitis C virus of claim 1, wherein the PRK2 inhibitor is administered in combination with the IFN-α.

* * * * *